(12) United States Patent
d'Arbelles

(10) Patent No.: US 6,286,682 B1
(45) Date of Patent: Sep. 11, 2001

(54) MEDICAL ALERT MESSAGE KIT

(75) Inventor: Rodolfo d'Arbelles, High Springs, FL (US)

(73) Assignee: Mywil, Inc., High Springs, FL (US)

( * ) Notice: Subject to any disclaimer, the term of this patent is extended or adjusted under 35 U.S.C. 154(b) by 0 days.

(21) Appl. No.: 09/412,533

(22) Filed: Oct. 5, 1999

Related U.S. Application Data

(60) Provisional application No. 60/103,038, filed on Oct. 5, 1998.

(51) Int. Cl.[7] .................................................. B65D 69/00
(52) U.S. Cl. ........................ 206/570; 206/572; 206/459.5
(58) Field of Search ............................... 206/570, 575, 206/459.5, 561, 572; 156/234, 240; 220/553, 555; 428/41.7, 42.1, 201; 607/95

(56) References Cited

U.S. PATENT DOCUMENTS

| | | | |
|---|---|---|---|
| 4,522,864 | * 6/1985 | Humason et al. | 428/201 |
| 4,594,276 | 6/1986 | Relyea . | |
| 4,788,971 | 12/1988 | Quisno . | |
| 5,257,721 | * 11/1993 | Smith et al. | 206/575 |
| 5,306,271 | 4/1994 | Zinreich et al. . | |
| 5,357,861 | 10/1994 | d'Arbelles et al. . | |
| 5,407,440 | 4/1995 | Zinreich et al. . | |
| 5,421,765 | * 6/1995 | Lehmann et al. | 446/901 |
| 5,470,351 | * 11/1995 | Ross et al. | 607/95 |
| 5,601,859 | 2/1997 | Penaluna . | |
| 5,743,899 | 4/1998 | Zinreich . | |
| 5,776,586 | 7/1998 | Lipper . | |
| 5,817,385 | * 10/1998 | Stanislav | 428/42.1 |
| 5,848,700 | * 12/1998 | Horn | 206/570 |
| 5,958,560 | * 9/1999 | Ewan | 428/201 |
| 5,979,658 | * 11/1999 | Allen et al. | 206/575 |

* cited by examiner

Primary Examiner—Luan K. Bui
(74) Attorney, Agent, or Firm—Saliwanchik, Lloyd & Saliwanchik

(57) ABSTRACT

A medical alert message kit containing medical stamp emblems to be applied to the human body for the purpose of communicating a medical condition or directive. The medical stamp emblem is releasably attached to a backing liner and includes a printed medical condition, message or image on a surface of porous, non-woven, compacted tissue substrate with an adhesive. The method includes applying the emblem on an area of medical interest readily observable by medical personnel.

8 Claims, 2 Drawing Sheets

MEDICAL ALERT MESSAGE KIT

CROSS-REFERENCE TO RELATED APPLICATIONS

This application claims priority from provisional application Ser. No. 60/103,038, filed Oct. 5, 1998, the disclosure of which is incorporated herein by reference in its entirety.

FIELD OF THE INVENTION

The present invention relates to a medical alert message emblem and kit and method of use.

BACKGROUND OF THE INVENTION

In recent years attention has been ever-increasingly drawn to the need for a system which allows a patient, who may or may not be capable of communicating, to alert medical staff of a pre-existing medical condition or of an advance directive regarding certain medical decisions, e.g., living wills. One such system is described in applicant's own U.S. Pat. No. 5,357,861 entitled "Medical Stamp System and Method of Use," incorporated herein by reference. This stamp system provides an ink stamp kit to be used by a physician in marking a patient with indicia for withholding extraordinary medical care after receiving appropriate authorization. However, due to certain regulations and concerns about re-using any product which has been in contact with a patient, there exists a need in the art for an alternative medical marking system to alleviate these concerns.

Another method for marking the skin of a patient is described in U.S. Pat. Nos. 5,306,271, 5,407,440, and 5,743,899 all to Zinreich et al., each incorporated herein by reference. This method provides for radiation therapy marking to delineate a radiation portal area on a patient's skin surface. The device includes a set of radiation therapy skin markers which are releasably attached to a backing liner and include an adhesive surface such that the markers may be releasably attached to a patient's skin surface. This marking method allows the tape-like markers to be readily removed (intentionally or accidentally) which then can lead to loss of the marker or re-adherence to an improper location or to another patient. Such type of markers are, therefore, unsuitable for medical alerts or advance directives which should be semi-permanent in nature and not reusable.

Accordingly, there is a need in the art for a medical alert message emblem, kit, and method which provides a plurality of one-time use semi-permanent skin markers for various messages, such as for pre-existing medical conditions or advance directives regarding certain medical decisions.

SUMMARY OF INVENTION

The present invention solves the needs in the art by providing a one-time use semi-permanent skin marker in the form of an adhesive substrate (similar to temporary tattoos) for various messages, such as for pre-existing medical conditions or advance directives regarding certain medical decisions. These medical stamp emblems can be used by a physician or other authorized personnel to allow a patient's body to communicate directions for any medical action or inaction, or medical message that the physician, medical staff person, or patient wishes to emphasize.

The medical stamp emblems are preferably made with FDA approved and certified hypo-allergenic inks. In storage, the temporary medical stamp emblems are releasably attached to a backing liner. The surface of the emblem consists of porous, non-woven, compacted tissue substrate with an adhesive on the backside of the substrate. The transferable image is made with FDA approved and certified hypo-allergenic inks. The image is reversed (mirror image) on the backing liner so as to be correctly viewed when applied to the skin.

The temporary medical stamp emblems are designed specifically for the purpose of alerting medical personnel (i.e., medics, physicians, surgeons, etc.) as to any action, inaction, or medical message that an individual or patient wishes to emphasize such as previously performed medical procedures and information concerning the patient's health or medical status. For example, the messages on the temporary medical stamp emblems may include, but are not limited to, ORGAN DONOR, DO NOT RESUSCITATE, ALLERGY ALERT, OPERATIVE SITE, SEIZURES, PACEMAKER, DIABETIC, HEART/LUNG/KIDNEY TRANSPLANT, BLOOD TYPE, ON BLOOD THINNER, and the like. Important messages will be placed over the heart, such as DNR (Do Not Resuscitate).

The medical stamp emblems may be separately packaged for individual sale or be provided in kit form. The medical alert kit can consist of: a holding container in the form of a box, a variety of medical emblems, a medical stamp applicator, a bottle containing rubbing alcohol, and an optional computer disk with medical and legal authorization forms. Placed on the inner top planar surface of the holding container could be various instructions or limited warranty statement in the form of a water-proof decal. A computer disk may also be placed there. The inner area of the box is preferably divided into six compartments (each holding a different item contained in the kit).

Also contained in the medical alert message kit is a medical emblem applicator which is used to transfer the appropriate medical message onto the skin.

A bottle of rubbing alcohol is also contained in the kit. The rubbing alcohol is used to clean the skin prior to application of the medical stamp emblem, and also for removal of the medical stamp emblem.

Finally, a computer disk (e.g., floppy, CD or other media) is also contained in the medic alert message kit. This disk contains all the necessary legal forms for each temporary medical stamp emblem contained in the kit. This kit will enable each medical institution, as well as each individual purchaser, to reproduce the forms and/or modify them according to their needs. Because the forms are customized and readily available time, money and paper will be saved. Additional information can also be provided in the kit, such as information concerning Advance Directives, information on Living Wills, Powers of Attorney, Surrogates, and various other information concerning legal rights and powers that patients have for decisions concerning their estate and management of their death.

The temporary medical stamp emblems can be applied anywhere on the body as is appropriate, using it (the body) as the media, thus providing assurance that the message it states will not get lost or overlooked in an emergency.

DETAILED DISCLOSURE OF THE INVENTION

Figure 1A:
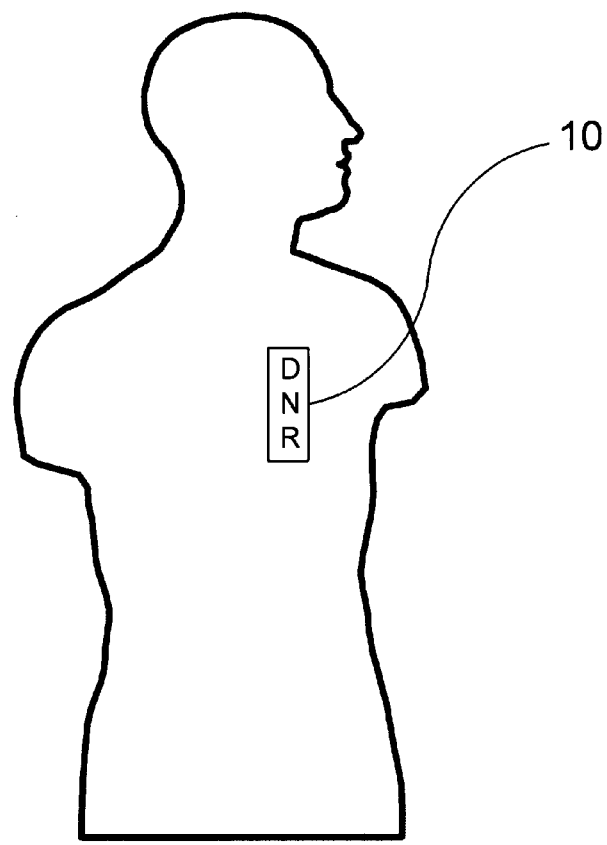
FIG. 1*a* is a sample medical stamp emblem of the present invention as applied to the patents skin.
Figure 1B:
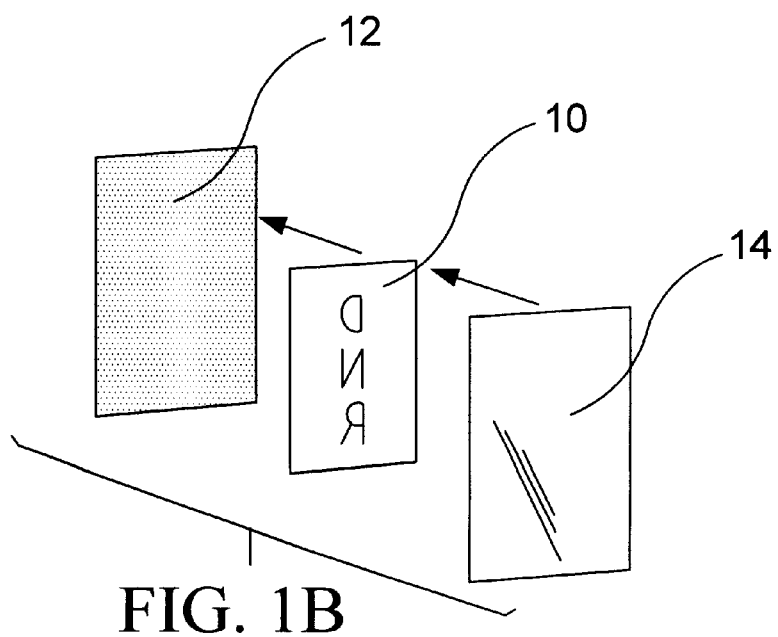
FIG. 1*b* is an expanded view of the stamp emblem.

The present invention solves the needs in the art by providing a plurality of one-time use semi-permanent skin markers in the form of a transferable image 10 (e.g., removable imitation tattoos) for various messages, such as for pre-existing medical conditions or advance directives regarding certain medical decisions. These medical stamp emblems 10 can be used by a physician or other authorized personnel in marking a patient's body as shown in FIG. 1a to communicate direction for any medical action or inaction, or medical message that the physician, medical staff person, or patient wishes to emphasize.

Various types of removable imitation body tattoos are well known in the art, albeit not for medical uses. Representative examples of the manufacture, materials and method of application of such tattoos are described, for example, in U.S. Pat. Nos. 4,594,276, 5,601,859, and 5,776,586, all of which are incorporated herein by reference. The three major types of removable tattoos include transferable dye images, painted images, and decal images. The present invention comprises all three types. Usually water-soluble dyes painted on a substrate in a pattern or image are transferred by wetting the pattern or image and then pressing the wetted dyes against the skin, transferring them to the skin. Decal tattoos comprise a printed image on a substrate with an adhesive material on the other side of the substrate.

The medical stamp emblems, in the form of tattoos, of the present invention are preferably made with FDA approved and certified hypo-allergenic inks. In a preferred embodiment, the temporary medical stamp emblems are releasably attached to a backing liner 12. The surface of the emblem consists of porous, non-woven, compacted tissue substrate with an adhesive on the backside of the substrate. The image 10 is made with FDA approved and certified hypo-allergenic inks, including, but not limited to, PVA CoPolymer, polyester resin, modified varnish, deodorized petroleum, silicon dioxide, aluminum silicate, iron oxide, FD&C yellow numbers 5 and 6 Aluminum lake, D&C red number 7 Lake, and FD&C blue number 1 Aluminum Lake. A transparent protective cover 14 is maintained on the surface of the image 10 which is removed prior to application. The image 10 is reverse (mirror image) on the backing liner 12 prior to application so as to be correctly viewable after application to the patient's skin.

The temporary medical stamp emblems of the present invention are designed specifically for the purpose of alerting medical personnel (i.e., medics, physicians, surgeons, etc.) as to any action, inaction, or medical message that an individual or patient wishes to emphasize such as previously performed medical procedures and information concerning the patient's health or medical status. For example, the messages on the temporary medical stamp emblems may include, but are not limited to, ORGAN DONOR, DO NOT RESUSCITATE, ALLERGY ALERT, OPERATIVE SITE, SEIZURES, PACEMAKER, DIABETIC, HEART/LUNG/KIDNEY TRANSPLANT, BLOOD TYPE, ON BLOOD THINNER, and the like. Important messages will be placed over the heart, such as DNR (Do Not Resuscitate).

Figure 2:
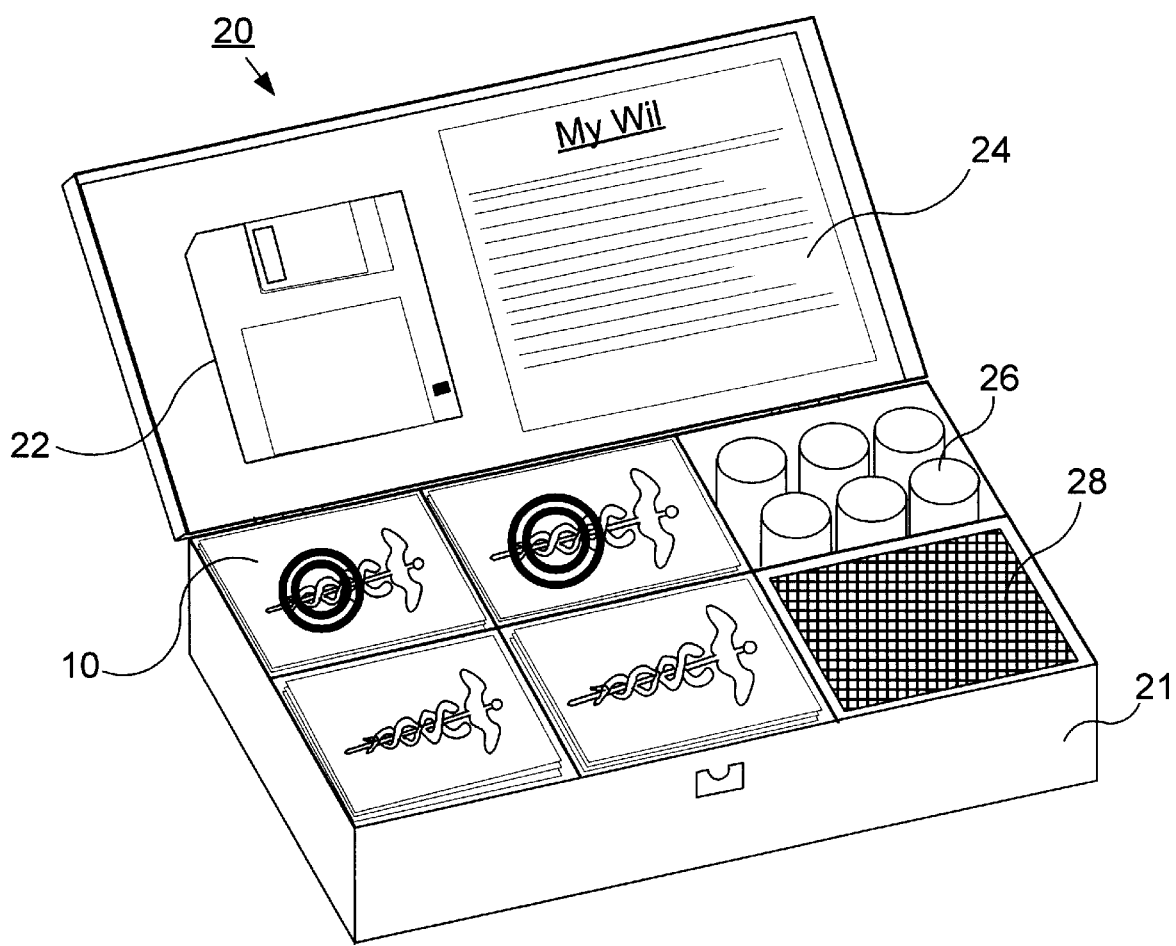
FIG. 2 is a prospective view of a preferred embodiment of the kit containing the medical stamp emblems of the present invention.

The medical stamp emblems 10 may be separately packaged for individual sale or be provided in kit form 20. In a preferred embodiment, the medical alert kit 20 of FIG. 2 consists of the following: a holding container in the form of a box 21, a variety of medical emblems 10, a medical stamp applicator 28, such gauze or cloth, either pre-moistened or wetted in use, bottle(s) containing rubbing alcohol 26 or other site preparation/cleaning substance and/or emblem removal substance, and an optional computer disk 22 with medical and legal authorization forms and instructions 24. The holding container 21 preferably comprises a box made either of wood or plastic which is preferably about thirteen inches long, six and a half inches wide and four and a quarter inches deep. However, the box can be customized to fit the individual needs of each medical institution or individual purchaser. To make the kit easily recognizable a decal containing the emblem(s) will be placed on the top planar surface of the box. Placed on the inner top planar surface of the holding container could be various instructions or limited warranty statement in the form of a water-proof decal 24. The computer disk 22 may also be placed there. The inner area of the box is preferably divided into six compartments (each holding a different item contained in the kit).

The medical emblem applicator 28 in the kit is used to transfer the appropriate medical message onto the skin. The applicator may be gauze or cloth which is either premoistened or wetted in use.

A bottle or a plurality of bottles of rubbing alcohol or other surface preparation substance 26 is also contained in the kit. In lieu of the bottles, pre-moistened towelettes containing the surface preparation substance may be used. The rubbing alcohol may be used to clean the skin prior to application of the medical stamp emblem, and also for removal of the medical stamp emblem.

Finally, a computer disk 22 (e.g., floppy, CD or other media) is also contained in the medic alert message kit. This disk contains all the necessary legal forms for each temporary medical stamp emblem contained in the kit. This kit will enable each medical institution, as well as each individual purchaser, to reproduce the forms and/or modify them according to their needs. Because the forms are customized and readily available time, money and paper will be saved. Additional information can also be provided in the kit, such as information concerning Advance Directives, information on Living Wills, Powers of Attorney, Surrogates, and various other information concerning legal rights and powers that patients have for decisions concerning their estate and management of their death.

The medical alert message kit, both the box and the contents thereof, may be customized to suit the needs of each medical institution and individual purchaser.

The use of the stamps will now be described. The temporary medical stamp emblems 10 can be applied anywhere on the body as is appropriate, using it (the body) as the media, thus providing assurance that the message it states will not get lost or overlooked in an emergency. Before the application process is initiated, the area on the skin where the temporary medical stamp emblem 10 is to be placed is cleaned with an appropriate substance such as alcohol 26, dried, and substantially free of hair. In certain cases, such as over the heart area, the area would be approximately three inches wide by four inches long (or 78 millimeters wide by 103 millimeters long) to provide sufficient room for the emblem. After the skin has been prepared, the person applying the emblem will remove the plastic protection sheet 14, being very careful not to touch the emblem 10 itself after the plastic has been removed. The emblem 10 should be placed on the prepared skin face down with firm pressure applied. Gauze 28, or a sponge, should then be saturated with water (at room temperature), and placed over the emblem 10 until thoroughly moistened, again applying firm pressure over the entire area. Sterile 4×4 gauze and sterile water should be used to prevent any untoward effects, i.e. infection. After waiting the appropriate time, about 30 seconds in most instances, the paper backing 12 may be removed by sliding or peeling it away from the emblem 10. The emblem and skin should then be rinsed with water and gently smoothed into place. The emblem 10 is generally dry in one to two minutes, and the process is complete.

The removal process includes soaking the entire area with isopropyl rubbing alcohol and allowing it to soak for at least 10 seconds so that the alcohol penetrates the inks. The emblem is then removed by gently rubbing the area repeatedly with gauze. Any residue left behind may then be removed completely with baby oil.

The emblem 10 may last up to two or three weeks or more. However, the emblem should be replaced every two to three weeks or when its message is no longer clear, whichever comes first.

Although particular and preferred embodiments of the present invention have been shown and described herein, it is to be understood that they can be modified without departing from the scope of the present invention, and all such modifications and equivalents are intended to be covered.

What is claimed is:

1. A medical alert kit to communicate direction for any medical action or inaction or medical message for selected patients comprising:

a container having divided compartments, said compartments individually housing:

a) a plurality of skin markers comprising a transferable image releasably attached to a backing liner, said image having a skin contact adhesive for applying said marker to at least one of the selected patient's skin;

b) a plurality of applicators for applying said skin marker to the patient's skin; and c) a skin preparation formula for preparing the patient's skin prior to application of the skin marker.

2. The kit of claim 1 wherein said transferable image comprises transferable dye.

3. The kit of claim 1 wherein said transferable image comprises transferable ink.

4. The kit of claim 1 wherein said transferable image comprises a transferable decal.

5. The kit of claim 1 wherein said transferable image comprises a transferable emblem of porous, non-woven, compacted tissue substrate having an inked image disposed thereon.

6. The kit of claim 5 wherein said inked image is hypo-allergenic.

7. The kit of claim 1 wherein said transferable image is applied to the skin over a patient's heart.

8. The kit of claim 1 wherein said transferable image is irrecoverable for reuse after application to a patient's skin.

* * * * *